(12) United States Patent
Kahn et al.

(10) Patent No.: US 7,396,361 B2
(45) Date of Patent: Jul. 8, 2008

(54) LIGHT TREATMENT HEAD

(76) Inventors: Fred Kahn, 65 Harbour Square Suite 1908, Toronto, Ontario (CA) M5J 1K6; Eli Hacco, 104 Fern Avenue, Toronto, Ontario (CA) M6R 1K3; Mark Anthony Peter Slonchka, 30 Allanhurst Crescent, Brampton, Ontario (CA) L6P 1C8

(*) Notice: Subject to any disclaimer, the term of this patent is extended or adjusted under 35 U.S.C. 154(b) by 0 days.

(21) Appl. No.: 11/785,192

(22) Filed: Apr. 16, 2007

(65) Prior Publication Data

US 2007/0255360 A1    Nov. 1, 2007

(51) Int. Cl.
    *A61N 5/06* (2006.01)
(52) U.S. Cl. .............................. 607/88; 607/89; 607/91

(58) Field of Classification Search ............. 607/88–91; 606/8–10, 22–31
See application file for complete search history.

(56) References Cited

U.S. PATENT DOCUMENTS

| 5,358,503 | A  | * | 10/1994 | Bertwell et al. ............... 606/27 |
| 5,616,140 | A  | * | 4/1997  | Prescott ....................... 606/10 |
| 6,221,095 | B1 | * | 4/2001  | Van Zuylen et al. ........... 607/88 |
| 6,596,016 | B1 | * | 7/2003  | Vreman et al. ................ 607/88 |
| 7,070,611 | B2 | * | 7/2006  | Biel ............................. 607/88 |

* cited by examiner

*Primary Examiner*—Ahmed M Farah

(57) ABSTRACT

A light treatment head which incorporates an array of light sources, a flexible power distribution panel, a plurality of heat sink bodies closely associated with the light sources, and a flexible housing enclosing the light sources, the distribution panel and the heat sink bodies.

4 Claims, 2 Drawing Sheets

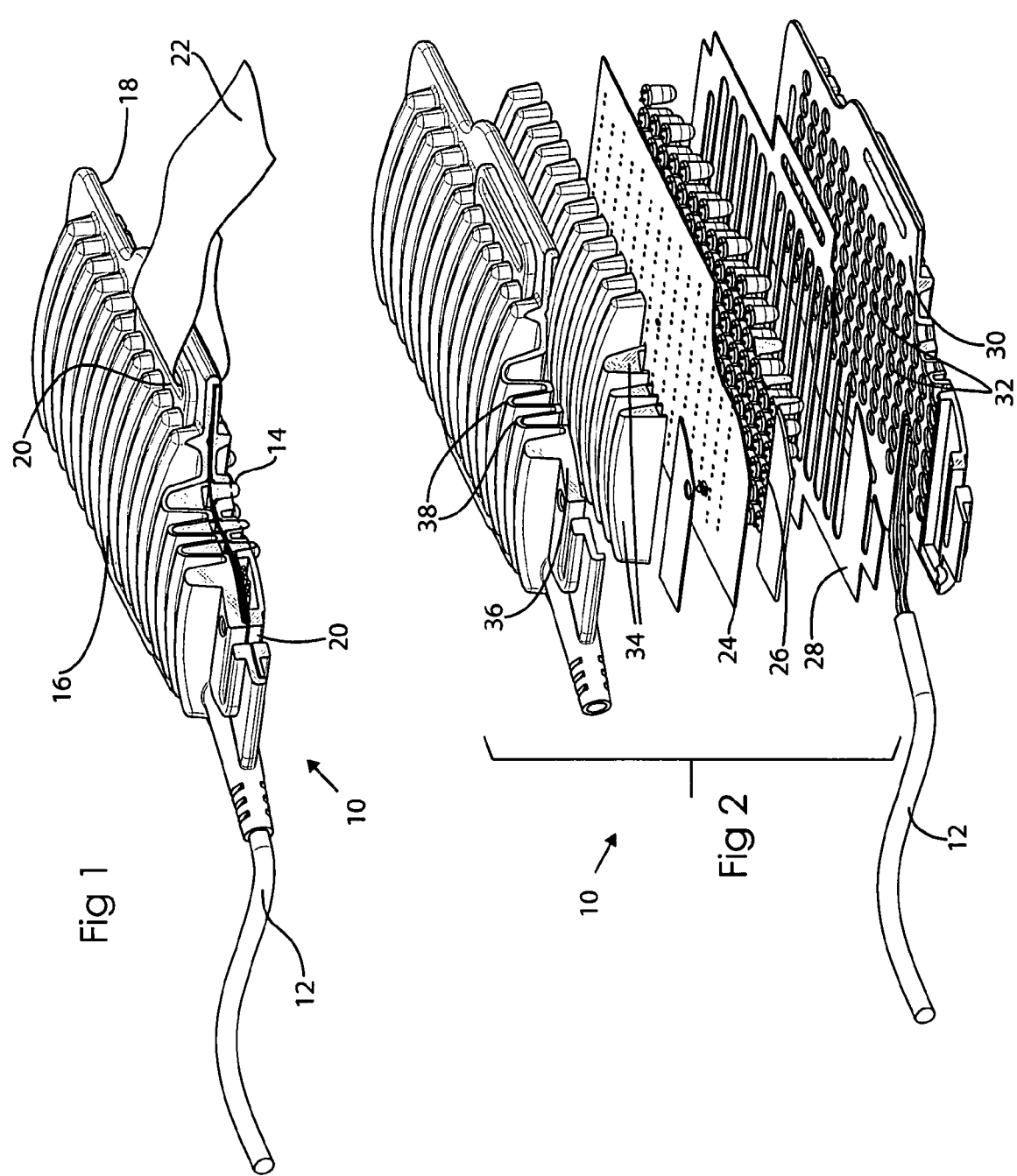

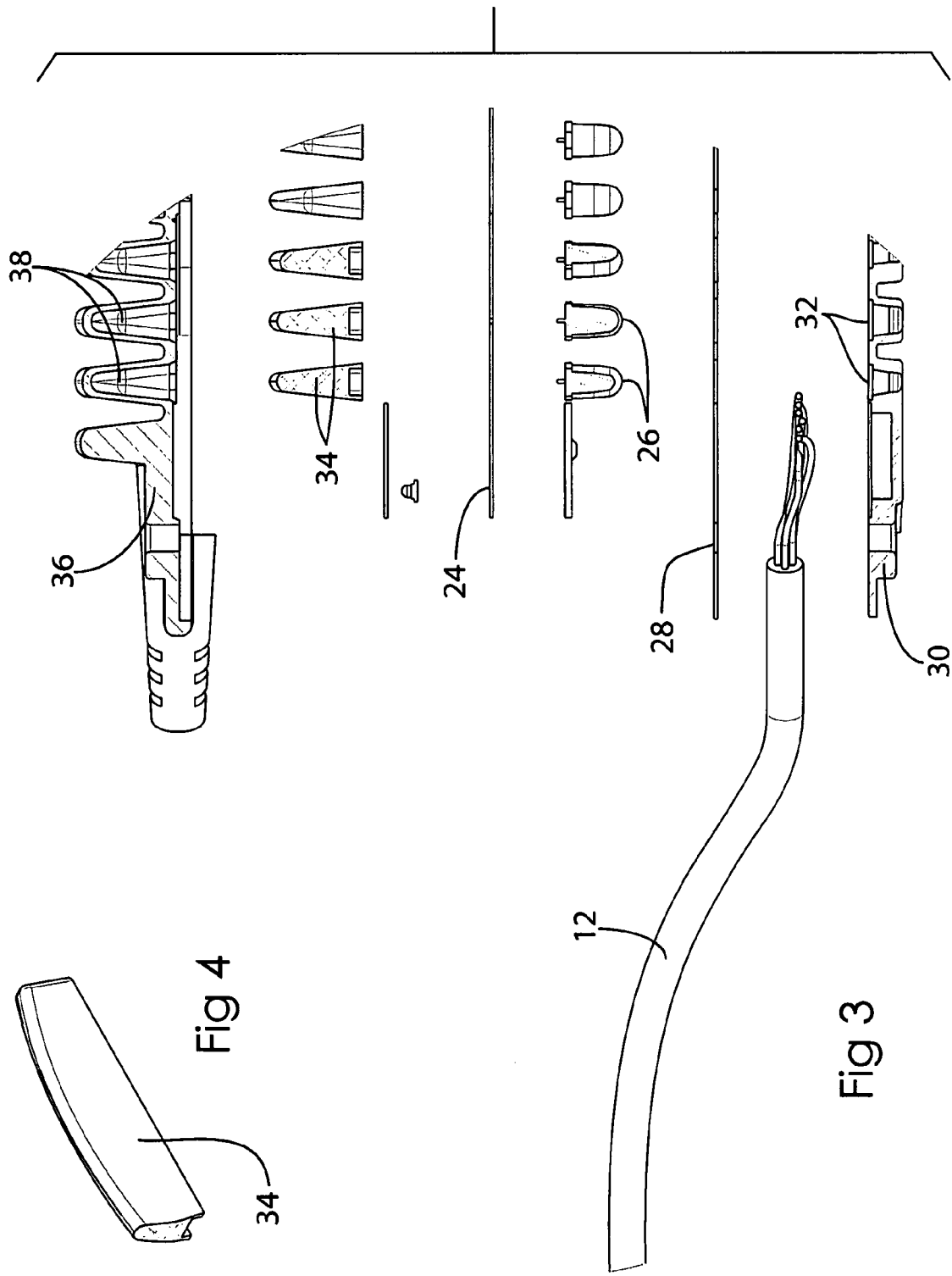

LIGHT TREATMENT HEAD

FIELD OF THE INVENTION

The invention relates to the field of light treatment therapy, and equipment for such therapy.

BACKGROUND OF THE INVENTION

Light treatment of patients for various conditions is becoming well known. Light treatment of injuries such as sport injuries, sprains and the like, light treatment of chronic conditions such as arthritis, sciatica and various related conditions, and light treatment of chronic slow healing wounds or sores, are all well known.

The principle of all these light treatments is the application of low intensity light radiating in the area of the patient's condition. It is found that in order to be effective, the light source should be close in contact with the skin. The light source is usually an array or panel of low intensity light emitting diodes, or in some cases low level laser. It is also found that the treatment becomes more effective over longer periods. The light sources are usually left in contact with the skin for thirty to sixty minutes in many cases. This ensures deep penetration of the light rays into the tissues, and produces the healing results experienced.

It is of course obvious that the light sources will develop heat. During the course of one application or treatment the heat developed by the light sources may become too great, and produces patient discomfort. It is then necessary to discontinue treatment for a moment, and exchange the one light treatment head with another, so that the treatment can continue. As a result of this light treatment in the past has been expensive. The need for providing multiple treatment heads for the treatment of each patient, significantly adds to the initial investment required to set up a clinic providing the treatment. Also, it is necessary to have paramedical or nursing assistants inspecting the various treatment stations regularly, to ensure that the patients are not suffering any discomfort from the treatment, and to change the treatment head before the patient suffers discomfort. This too adds to the cost of the treatment and the operation of the clinic. Clearly it is desirable to provide a light treatment head for this type of treatment which is capable of dissipating at least some of the heat generated by the light sources, and treatment heads also that are of such a design that they can be manufactured at a more reasonable cost.

Another factor in the design of such treatment head is that the treatment is preferably applied over a fairly large area of the body. Light treatment heads usually measure about four inches by ten inches, but could be even bigger if a suitable design was available. In order to provide a light treatment head of this large footprint, it is desirable to make the treatment head flexible. This ensures that the light sources in the light treatment head can all lie in contact with the skin, with the light treatment head flexing and conforming to the shape of the body.

BRIEF SUMMARY OF THE INVENTION

The invention provides a light treatment head which incorporates an array of light sources, in a flexible contact distribution network board, and incorporating a plurality of heat sink bodies closely associated with the light sources, and a flexible housing for enclosing the light sources, the distribution board and the heat sinks.

Preferably there will be a flexible face panel formed with a plurality of holes for receiving light sources, and a plurality of individual heat sink bodies are provided.

Preferably there will be a back panel provided, overlying the heat sink bodies.

Preferably the back panel and the face panel are bonded together around the flanges.

Preferably the heat sink bodies are typically secured in the recesses by adhesive.

Preferably the heat sink body recesses are formed in the back panel and thus form an array of fin like bodies, with air spaces between them, and defining a substantial surface area in contact with the air.

Preferably the face panel and back panel are formed of synthetic flexible material, such as a silicon type material which can be moulded to the desired shape, and which can be subjected to heat, and which will remain flexible.

IN THE DRAWINGS

FIG. 1 is a perspective illustration of a light treatment head illustrating the invention;

FIG. 2 is an exploded perspective of FIG. 1;

FIG. 3 is a section corresponding of the treatment head exploded; and,

FIG. 4 is a perspective illustration of a typical heat sink body.

DESCRIPTION OF A SPECIFIC EMBODIMENT

A typical light treatment head illustrating invention is shown as (10) in FIG. 1. The treatment head will be seen to be of rectangular shape, and having a connection cable (12) extending from one corner for convenience. The treatment head has a light source side (14), and a heat sink side (16) opposite to the light source side.

Edge flanges (18) may advantageously be arranged around the edge of the head, and slots (20) may be formed in such flanges. Any suitable form of attachment straps (22) can be slipped through the slots, so that the treatment head can be temporarily secured in a location on a patient's body.

As shown in FIG. 2, the treatment head is made up of a light source circuit panel (24), provided with wiring suitable for supplying a plurality of light sources (26). An intermediate non-conductive panel (28) is located beneath the panel (24). A flexible face panel (30) is formed with a plurality of holes (32) for receiving light sources (26). A plurality of individual heat sink bodies (34) are provided. The heat sink bodies (34) are in this case formed of aluminum, or other metal having suitable heat transfer properties may be used. They are preferably formed, in section, in the shape of elongated wedges, so as to provided for ease of assembly (FIG. 4).

A back panel (36) is provided, overlying the heat sink bodies (34). The back panel (36) and the face panel (30) are bonded together around the flanges (18) by any suitable adhesive or chemical bonding agent, or by heat sealing.

The back panel (36) is formed with a plurality of heat sink body recesses (38), defining recesses shaped to fit and receive individual heat sink bodies (34). The heat sink bodies (34) are typically secured in the recesses (38) by adhesive. The heat sink body recesses (38) are formed in the back panel (36) and thus form an array of fin like bodies, with air spaces between them, and defining a substantial surface area in contact with the air. In this way heat can be transferred from the heat sink bodies (34), through the back panel (36), to atmosphere, and thus dissipated from the treatment head.

The face panel (30) and back panel (36) are preferably formed of synthetic flexible material, such as a silicon type material which can be moulded to the desired shape, and which can be subjected to heat, and which will remain flexible.

When power is supplied to the light circuit panel (24), the lights (26) in the array attached to the panel are illuminated. When the treatment head is placed in contact with the skin, some of the heat generated by the lights will be transferred through circuit panel (24) to the heat sink bodies (34). As these heat sink bodies (34) heat up, some heat from them will be re-radiated or conducted to the exterior of the back panel (36), and will be dissipated from the back panel (36) by radiation and convection. This will assist in avoiding excessive heat from the lights being applied to the skin.

The material from which the face panel (30) and the back panel (36) are made is flexible, and allows the treatment head to fold around and lie against an area of the body to be treated.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. A light treatment head for the application of light therapy to a living body, and comprising;
   a flexible power distribution board,
   a plurality of light sources connected to said board;
   a plurality of individual separate heat sink bodies closely associated with the light sources;
   a flexible housing for enclosing the light sources, the distribution board and the plurality of individual separate heat sink bodies in turn comprising:
   a flexible face panel formed with a plurality of holes for receiving said light sources;
   a flexible back panel overlying all said individual separate heat sink bodies;
   a plurality of heat sink body recesses formed in said back panel and shaped to receive respective said individual separate heat sink bodies and forming an array of fin like bodies; and,
   free air spaces defined between said fin like bodies on the exterior of said back panel, to permit air circulation between and around said fin like bodies thereby dissipating heat from said heat sink bodies.

2. A light treatment head for the application of light therapy to a living body, as claimed in claim 1, including edge flanges formed around the back panel of said flexible housing and the face panel of said flexible housing, said edge flanges being bonded together around said housing.

3. A light treatment head for the application of light therapy to a living body, as claimed in claim 1 wherein said heat sink bodies are secured in said recesses by adhesive.

4. A light treatment head for the application of light therapy to a living body, as claimed in claim 1 wherein said face panel and back panel are formed of synthetic flexible material, selected from the group of silicon type materials which can be moulded to the desired shape, and which can be subjected to heat, and which will remain flexible, said face panel and said back panel being bonded together around said board and said light sources and said heat sink bodies.

* * * * *